US00PP26226P3

(12) United States Plant Patent
Van Dijk

(10) Patent No.: US PP26,226 P3
(45) Date of Patent: Dec. 15, 2015

(54) *ANTHURIUM* PLANT NAMED 'ANTHDOZAL'

(50) Latin Name: ***Anthurium andreanum* L.**
Varietal Denomination: ANTHDOZAL

(71) Applicant: ANTHURA B.V., Bleiswijk (NL)

(72) Inventor: Jan Van Dijk, Bleiswijk (NL)

(73) Assignee: ANTHURA B.V., Bleiswijk (NL)

( * ) Notice: Subject to any disclaimer, the term of this patent is extended or adjusted under 35 U.S.C. 154(b) by 109 days.

(21) Appl. No.: 13/999,931

(22) Filed: Apr. 4, 2014

(65) Prior Publication Data

US 2015/0289432 P1 Oct. 8, 2015

(51) Int. Cl.
*A01H 5/02* (2006.01)

(52) U.S. Cl.
USPC ..... Plt./367

(58) Field of Classification Search
USPC ..... Plt./365, 367
See application file for complete search history.

*Primary Examiner* — Susan McCormick Ewoldt
(74) *Attorney, Agent, or Firm* — Jondle & Associates, P.C.

(57) ABSTRACT

A new and distinct variety of *Anthurium* plant named 'ANTHDOZAL' particularly characterized by having glossy pink, durable spathes, green, durable leaves, strong shoot formation, flowers continuously throughout the year, a compact and full plant habit and a plant height of 30 cm to 35 cm, is disclosed.

1 Drawing Sheet

Genus and species: *Anthurium andreanum* L.
Variety denomination: 'ANTHDOZAL'.

BACKGROUND OF THE NEW PLANT

The present invention comprises a new and distinct variety of *Anthurium*, botanically known as *Anthurium andreanum* L., and hereinafter referred to by the variety name 'ANTHDOZAL'. The new variety originated from a naturally occurring, single plant mutation in a greenhouse in a production clone of 'ANTHEPEDI' (U.S. Plant Pat. No. 18,644) in Bleiswijk, The Netherlands. The original variety is a red *Anthurium* pot plant designated 'ANTHEPEDI'.

A single plant was selected in January 2006 and has been asexually reproduced repeatedly by tissue culture in Bleiswijk, The Netherlands over a five-year period. The present invention has been found to retain its distinctive characteristics through successive asexual propagations.

Plant Breeder's Rights for this variety have been applied for in Europe on Apr. 25, 2013. 'ANTHDOZAL' has not been made publicly available or sold anywhere in the world more than one year prior to the filing of this application.

SUMMARY OF THE INVENTION

The following are the most outstanding and distinguishing characteristics of this new variety when grown under normal horticultural practices in Bleiswijk, The Netherlands.

1) Pink spathes;
2) White spadix;
3) Rich shoot formation;
4) Compact plant habit; and
5) Green foliage.

DESCRIPTION OF THE PHOTOGRAPH

This new *Anthurium* plant is illustrated by the accompanying photograph which shows the overall plant habit including blooms, buds and foliage of the plant; the colors shown are as true as can be reasonably obtained by conventional photographic procedures.

The photograph is of a 60-week old plant grown in a greenhouse in Bleiswijk, The Netherlands in 2014.

DESCRIPTION OF THE NEW VARIETY

The following detailed description sets forth the distinctive characteristics of 'ANTHDOZAL'. The data which define these characteristics were collected from asexual reproductions carried out in Bleiswijk, The Netherlands. The plant history was taken on 60-week old plants which were planted from tissue culture in 14-cm pots and grown in a glass greenhouse between 19° C. and 24° C. Observations were made in February 2014. Color readings were taken under 5000 lux natural light in the greenhouse: Color references are primarily to The R.H.S. Colour Chart of The Royal Horticultural Society of London (R.H.S.) (2001).

DETAILED BOTANICAL DESCRIPTION

Classification:
- *Family.*—Araceae.
- *Botanical.*—*Anthurium andreanum* L.
- *Common name.*—*Anthurium.*
- *Denomination.*—'ANTHDOZAL'.

Parentage:
- *Natural mutation parent.*—'ANTHEPEDI' (U.S. Plant Pat. No. 18,644).

Propagation:
- *Propagation.*—Tissue culture.
- *Root description.*—Cream white-colored roots with hairy lateral roots having yellow-colored root tips.
- *Time to produce a finished flowering plant.*—60 to 70 weeks for a 14 cm pot.

Plant:
- *Growth habit.*—Herbaceous perennial.
- *Height* (*measured from soil, including inflorescence*).—30.0 cm to 35.0 cm.
- *Width* (*measured from leaf tips*).—30.0 cm to 35.0 cm.

Leaves:

*Immature leaves.*—Length: 4.0 cm to 9.0 cm. Width: 2.5 cm to 6.0 cm. Color: Upper surface: RHS 138A. Lower surface: RHS 138A. Texture (both upper and lower surfaces): Shiny.

*Mature leaves.*—Length (fully expanded): 13.0 cm to 20.0 cm. Width: 8.0 cm to 13.0 cm. Shape: Ovate. Apex: Acuminate. Base: Free lobes. Leaf blade angle with the petiole: Between 70 degrees and 110 degrees. Leaf margin: Entire. Color: Upper surface: RHS 139A. Lower surface: RHS 137B. Texture: Smooth. Venation: The veins protrude at the underside of the leaves. Venation color: Upper surface: RHS 137C. Lower surface: RHS 146D.

*Lobes.*—Arrangement: Free. Length of lobes of mature leaf blades: 2.0 cm to 4.0 cm. Width of lobes of mature leaf blades: 3.0 cm to 6.0 cm. Distance from petiole/leaf junction to highest point on lobes of mature leaf blades: 3.0 cm to 5.0 cm.

*Petiole.*—Cross-section: Round. Diameter: 0.3 cm to 0.4 cm. Length: 14.0 cm to 20.0 cm for a mature leaf size. Color: Mature leaf: RHS 137B. Immature leaf: RHS 146C. Cataphyl color surrounding the petiole: Outside: RHS 146C. Inside: RHS 146D.

*Geniculum.*—Length: 1.0 cm to 2.0 cm. Width: 0.3 cm to 0.4 cm. Color: RHS 137B.

Inflorescence:

*Arrangement.*—At same level or just above the leaf canopy.

*Flowering habit (length of flowering season).*—Continuous.

*Number of inflorescences per plant.*—6 to 10.

*Fragrance.*—Absent.

*Longevity of inflorescence on plant.*—More than a year.

*Longevity of the flower as a cutflower.*—Not observed.

Spathe:

*Arrangement.*—Spathe angle with the peduncle is between 80 degrees and 100 degrees; the spathe stands on a wiry peduncle about 0 cm to 5 cm above the foliage.

*Shape.*—Ovate.

*Apex.*—Broad acuminate.

*Base.*—Free lobes.

*Texture.*—Slightly blistered and glossy.

*Margin.*—Entire.

*Size.*—Height: 15.0 cm to 25.0 cm (Peduncle length at maturity). Length: 6.0 cm to 9.0 cm. Width: 7.0 cm to 11.0 cm.

*Color.*—Just fully open: Upper surface: RHS 52A. Lower surface: RHS 51B. 2 to 4 weeks after opening (Upper surface): RHS 52A. 8 to 12 weeks after opening (Upper surface): RHS 53A, very slowly discoloring further as the spathe ages.

Peduncle:

*Shape.*—Wiry.

*Cross-section.*—Round.

*Length.*—15.0 cm to 25.0 cm.

*Diameter.*—0.3 cm to 0.4 cm.

*Color.*—RHS 146B and remaining that color when aging.

Flowering time:

*General.*—One small rooted untreated tissue culture plant of 4 cm tall will flower after 6 to 8 months, depending on the season, and 2 to 4 blossoms appear. More blossoms appear after some additional weeks so that a full flowering and commercial plant will have 6 to 8 pink spathes. Smaller blossoms may occur on less mature plants.

Spadix:

*Size.*—Length: 2.0 cm to 4.0 cm (depending on flower size). Width (at apex): 0.5 cm to 0.7 cm. Width (at base): 0.6 cm to 0.8 cm.

*Shape.*—Columnar.

*Angle from spadix tip to peduncle.*—170 degrees (spadix is in one line with peduncle).

*Texture.*—When the spathe is unfurling the spadix is smooth. When the spadix matures, very small stigmata protrude. The stigmata are evenly distributed round the spadix. The spadix matures from base to top, slowly giving the spadix a somewhat coarse appearance.

*Color.*—Immature: RHS 153D. Mature: RHS 155A. Ages to: RHS 145A.

Flowers:

*Quantity per spadix.*—50 to 150.

*Spadix flower arrangement.*—Bisexual, rounded in cross-section.

*Shape.*—Small.

*Size.*—Length: 0.2 cm to 0.3 cm. Diameter (maximum): 0.2 cm.

*Color.*—RHS 155A.

Reproductive organs:

*Stamens.*—Anthers and filaments are not clearly visible.

*Pollen amount.*—Very little.

*Pollen color.*—RHS 155A.

*Pistil.*—Length: Less than 0.01 cm. Color: RHS 155A.

*Style.*—Very small.

*Stigma.*—Shape: Round and very small. Diameter: Less than 0.1 cm. Color: RHS 155A.

*Ovary.*—Not observed.

*Ovary color.*—Not observed.

Fruit and seed set: Seed production has not been observed to date.

COMPARISON WITH PARENTAL AND COMMERCIAL VARIETIES

'ANTHDOZAL' differs from the natural mutation parent and commercial variety 'ANTHEPEDI' (U.S. Plant Pat. No. 18,644) in that 'ANTHDOZAL' has pink spathes (RHS 52A), whereas 'ANTHEPEDI' has red spathes (RHS 45B).

'ANTHDOZAL' differs from commercial variety 'ANTHCORYO' (unpatented) in that 'ANTHDOZAL' has stronger shoot formation and slightly blistered spathes, whereas 'ANTHCORYO' has weak shoot formation and unblistered spathes.

'ANTHDOZAL' can be compared to commercial varieties *Anthurium* 'ANTHEPEDI' (U.S. Plant Pat. No. 18,644) and 'ANTHCORYO' (unpatented). Additional comparison data is shown in Table 1 below.

TABLE 1

Comparison of characteristics between 'ANTHDOZAL', 'ANTHEPEDI' and 'ANTHCORYO'

| Characteristic | 'ANTHDOZAL' | 'ANTHEPEDI' | 'ANTHCORYO' |
|---|---|---|---|
| Spathe colour | Strong | Strong | Weak |
| Spadix colour | RHS 52A | RHS 45B | RHS 51A |
| Spathe blistering | Weak | Weak | Absent |

I claim:

1. A new and distinct variety of *Anthurium* plant named 'ANTHDOZAL' as shown and described herein.

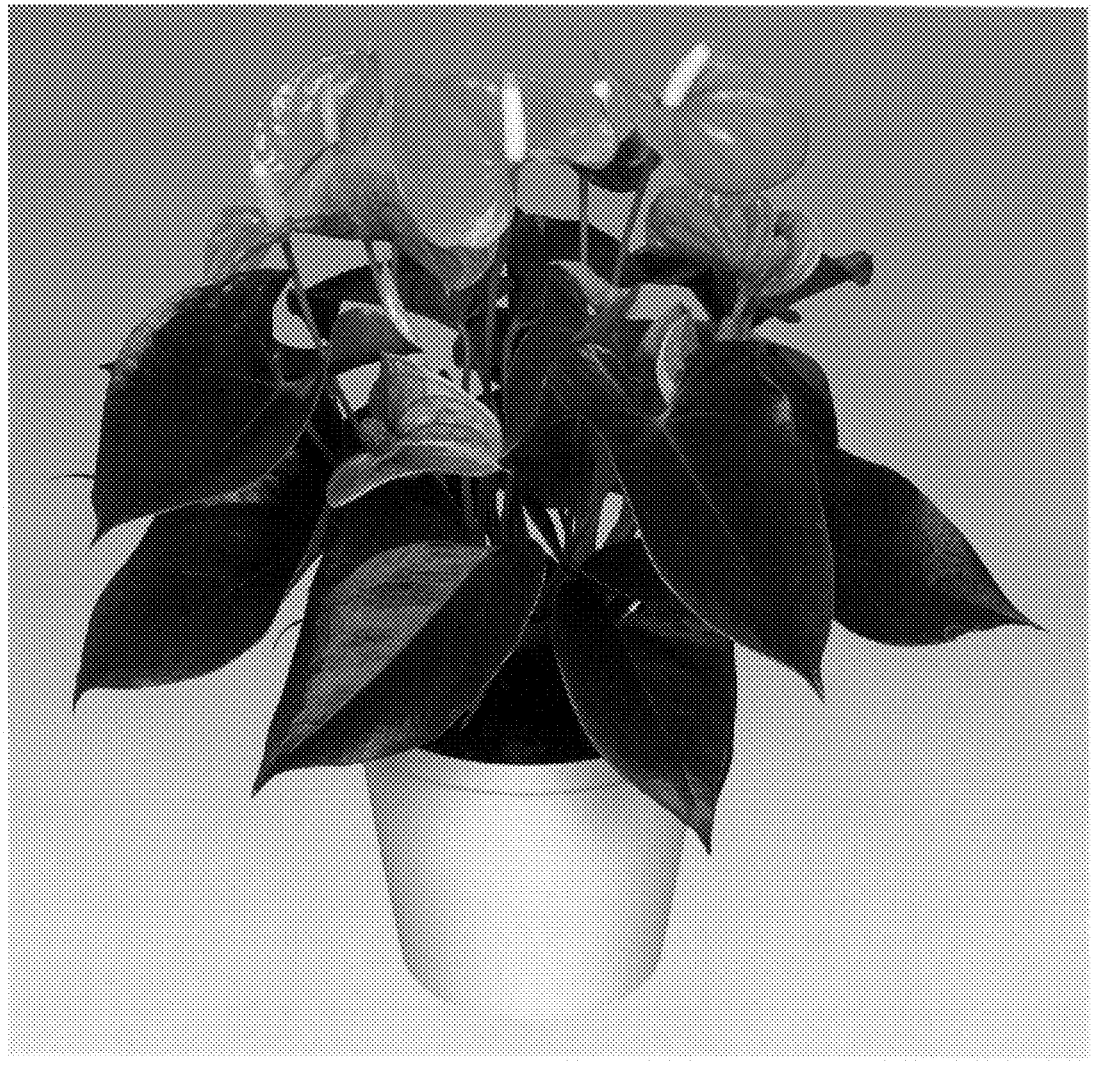

* * * * *